(12) United States Patent
Sexton et al.

(10) Patent No.: US 7,827,983 B2
(45) Date of Patent: Nov. 9, 2010

(54) METHOD FOR MAKING A PHARMACEUTICALLY ACTIVE INGREDIENT ABUSE-PREVENTION DEVICE

(75) Inventors: Douglas A. Sexton, La Jolla, CA (US); Winthrop D. Childers, San Diego, CA (US)

(73) Assignee: Hewlett-Packard Development Company, L.P., Houston, TX (US)

(*) Notice: Subject to any disclaimer, the term of this patent is extended or adjusted under 35 U.S.C. 154(b) by 1723 days.

(21) Appl. No.: 11/017,347

(22) Filed: Dec. 20, 2004

(65) Prior Publication Data
US 2006/0130828 A1 Jun. 22, 2006

(51) Int. Cl.
*A61M 11/00* (2006.01)
*F16K 31/02* (2006.01)
*A62B 9/00* (2006.01)

(52) U.S. Cl. ............... 128/200.23; 128/200.14; 128/200.16; 128/204.21; 128/204.23; 128/205.23; 128/202.22

(58) Field of Classification Search ............ 128/200.14, 128/200.16, 200.23, 204.21, 204.23, 205.23, 128/202.22
See application file for complete search history.

(56) References Cited

U.S. PATENT DOCUMENTS

| | | | |
|---|---|---|---|
| 3,255,872 A | 6/1966 | Long et al. | |
| 3,756,389 A | 9/1973 | Firth | |
| 4,226,330 A | 10/1980 | Butler | |
| 4,632,244 A | 12/1986 | Landau | |
| 4,856,651 A | 8/1989 | Francis, Jr. | |
| 4,994,056 A | 2/1991 | Ikeda | |
| 5,149,538 A | 9/1992 | Granger et al. | |
| 5,236,714 A | 8/1993 | Lee et al. | |
| 5,284,275 A | 2/1994 | Shomer | |
| 5,431,496 A | 7/1995 | Balteau et al. | |
| 6,036,004 A | 3/2000 | Bowen | |
| 6,062,213 A | 5/2000 | Fuisz et al. | |
| 6,098,620 A | 8/2000 | Lloyd et al. | |
| 6,114,658 A | 9/2000 | Roth et al. | |
| 6,247,485 B1 | 6/2001 | Rossi et al. | |
| 6,529,446 B1 | 3/2003 | de la Huerga | |
| 6,546,281 B1 | 4/2003 | Zhang et al. | |
| 6,569,449 B1 | 5/2003 | Stinchcomb et al. | |
| 6,607,696 B1 | 8/2003 | Hamilton et al. | |
| 6,615,825 B2 | 9/2003 | Stenzler | |
| 6,627,635 B2 | 9/2003 | Palermo et al. | |
| 6,669,683 B2 | 12/2003 | Santini, Jr. et al. | |
| 6,684,880 B2 | 2/2004 | Trueba | |
| 6,696,088 B2 | 2/2004 | Oshlack et al. | |

(Continued)

FOREIGN PATENT DOCUMENTS

WO    WO 2004/030525    4/2004

(Continued)

*Primary Examiner*—Patricia M Bianco
*Assistant Examiner*—Nihir Patel

(57) ABSTRACT

A method of making a pharmaceutically active ingredient abuse-prevention device includes providing a pharmaceutically active ingredient and providing an antagonist of the pharmaceutically active ingredient. The antagonist is in selective fluid communication with the pharmaceutically active ingredient. Electronic circuitry is configured to selectively operate the fluid communication between the antagonist and the pharmaceutically active ingredient so as to mix the pharmaceutically active ingredient with the antagonist upon recognition of one or more predetermined fault conditions. Mixing the pharmaceutically active ingredient with the antagonist renders the pharmaceutically active ingredient substantially ineffective.

28 Claims, 4 Drawing Sheets

U.S. PATENT DOCUMENTS

| | | |
|---|---|---|
| 6,755,189 B2 | 6/2004 | Ivri et al. |
| 6,776,978 B2 | 8/2004 | Rabinowitz et al. |
| 7,182,955 B2 * | 2/2007 | Hart et al. .................. 424/449 |
| 7,198,044 B2 * | 4/2007 | Trueba .................. 128/200.16 |
| 2003/0065002 A1 | 4/2003 | Caruso et al. |
| 2003/0091635 A1 | 5/2003 | Baichwal et al. |
| 2003/0183226 A1 | 10/2003 | Brand et al. |
| 2003/0183228 A1 | 10/2003 | Clark |
| 2003/0191147 A1 | 10/2003 | Sherman et al. |
| 2003/0221108 A1 | 11/2003 | Rupp |
| 2003/0234187 A1 | 12/2003 | Paxton et al. |
| 2004/0013716 A1 | 1/2004 | Gale et al. |
| 2004/0084044 A1 | 5/2004 | Childers et al. |
| 2004/0109886 A1 | 6/2004 | Rigby |
| 2004/0126323 A1 | 7/2004 | Shevchuk et al. |
| 2004/0170567 A1 | 9/2004 | Sackler |
| 2004/0197274 A1 | 10/2004 | Fein et al. |

FOREIGN PATENT DOCUMENTS

| | | |
|---|---|---|
| WO | WO 2005/061033 | 7/2005 |

* cited by examiner

```
                    ┌─────────────────┐
                    │ RECEIVING FIRST │
                    │    BIOMETRIC    │──── 31
                    │   INFORMATION   │
                    └────────┬────────┘
                             │
                             ▼
                    ┌─────────────────┐
                    │ ACTIVATION SIGNAL│──── 33
                    │     RECEIVED    │
                    └────────┬────────┘
                             │
                             ▼
                    ┌─────────────────┐
                    │ SECOND BIOMETRIC│
                    │   INFORMATION   │──── 35
                    │     RECEIVED    │
                    └────────┬────────┘
                             │
                             ▼
                          ╱─────╲ ──── 37
            39      NO  ╱ PROPER ╲   YES    41
             ╲        ╱COMPARISON ╲        ╱
              ╲──────╱BETWEEN FIRST╲──────╱
                     ╲  AND SECOND ╱
                     ╲  BIOMETRIC ╱
                      ╲    ?    ╱
                       ╲───────╱
     ┌──────────────┐                ┌──────────────┐
     │FAULT CONDITION│                │GENERATE AEROSOL│
     │SIGNAL IMPARTED│                │  OF MEDICANT  │
     └───────┬──────┘                └──────────────┘
             │
             ▼
     ┌──────────────┐
     │ACTIVATE MIXING OF│
     │ANTAGONIST WITH │──── 43
     │   MEDICANT    │
     └──────────────┘
```

*Figure 5*

METHOD FOR MAKING A PHARMACEUTICALLY ACTIVE INGREDIENT ABUSE-PREVENTION DEVICE

BACKGROUND

The present disclosure relates generally to pharmaceutically active ingredients and more particularly to a method of making a pharmaceutically active ingredient abuse-prevention device.

Pharmaceutically active ingredients may include various drugs that exhibit opium or morphine-like properties, such as, for example opioids. Opioids are often administered to patients as analgesics, but have many other pharmacological effects, including drowsiness, respiratory depression, mood swings, and mental clouding without loss of consciousness. Opioids act as agonists as they interact with stereospecific and saturable binding sites in the brain and other tissues. Endogenous opioid-like peptides may be present in areas of the central nervous system that may be related to pain perception, movement, mood, behavior, and the regulation of neuroendocrinological functions. Opium contains more than twenty distinct alkaloids, including morphine, codeine and papaverine.

Repeated opioid use may lead to the development of tolerance, physical dependence, and/or psychological dependence (i.e., addiction) thereon. A concern in using opioids for the treatment of pain is the potential development of such tolerance and/or addiction. Another major concern is the transportation of these drugs from the patient to a non-patient for recreational purposes.

Opioid antagonists have been developed to block or reverse the effects of opioid agonists. Opioid antagonists have been used as once-a-day treatments to substantially block the euphoric effects that might be otherwise obtained upon administration of opioids to addicts. While small doses of antagonists may be used to determine whether an individual is physically dependent on a drug, more commonly, antagonists are used to reverse the effects of drugs on individuals who have overdosed.

There have previously been attempts to control the potential abuse of opioids. Particular doses of opioids may be more potent when administered parenterally than when administered orally. Attempts to reduce or prevent abuse have included adding an antagonist to the oral dosage form which is not orally active but which will substantially block the analgesic/euphoric effects of the opioid if an attempt is made to dissolve the opioid and administer it parenterally.

Attempts have also been made to control the potential abuse of opioids contained within inhalation systems. These attempts include some form of "lock and key" to allow a certain patient access to the opioid. However, the potential of abuse remains, as the keys could be shared with others or the device could be tampered with in an attempt to remove the opioid.

As such, it would be desirable to provide an inhalation system that substantially prevents abuse of a pharmaceutically active ingredient contained therein.

SUMMARY

A method of making a pharmaceutically active ingredient abuse-prevention device is disclosed. The method includes providing a pharmaceutically active ingredient and an antagonist of the pharmaceutically active ingredient. The antagonist is in selective fluid communication with the pharmaceutically active ingredient. Electronic circuitry is configured to selectively operate the fluid communication between the antagonist and the pharmaceutically active ingredient so as to mix the pharmaceutically active ingredient with the antagonist upon recognition of one or more predetermined fault conditions. Mixing the pharmaceutically active ingredient with the antagonist renders the pharmaceutically active ingredient substantially ineffective.

BRIEF DESCRIPTION OF THE DRAWINGS

Objects, features and advantages will become apparent by reference to the following detailed description and drawings, in which like reference numerals correspond to similar, though not necessarily identical components. For the sake of brevity, reference numerals having a previously described function may not necessarily be described in connection with subsequent drawings in which they appear.

FIG. 5 is a flow diagram depicting an embodiment of a method as disclosed herein;

DETAILED DESCRIPTION

Embodiments of the present disclosure advantageously provide a method for preventing abuse of a pharmaceutically active ingredients (non-limitative examples of which include medicants and opioids). The method generally includes providing a pharmaceutically active ingredient and an antagonist of the pharmaceutically active ingredient, such that the antagonist is in selective fluid communication with the pharmaceutically active ingredient. The fluid communication is advantageously selectively controlled such that, upon exposure to and/or recognition of certain fault conditions, the pharmaceutically active ingredient and antagonist are mixed. As such, the selective fluid communication allows the pharmaceutically active ingredient to be rendered substantially ineffective when, for example, the pharmaceutically active ingredient has expired, an unauthorized user attempts to use the pharmaceutically active ingredient, and/or someone attempts to abuse the pharmaceutically active ingredient. It is to be understood that when the pharmaceutically active ingredient is rendered substantially ineffective, the antagonist counteracts the effects of the pharmaceutically active ingredient such that the user is advantageously prevented from potentially abusing the pharmaceutically active ingredient.

Alternate embodiment(s) include drop-generating technology in mixing the antagonist with the pharmaceutically active agent. A system for preventing pharmaceutically active ingredient abuse and an inhaler incorporating the various embodiments of the system are also disclosed herein.

Figure 1:
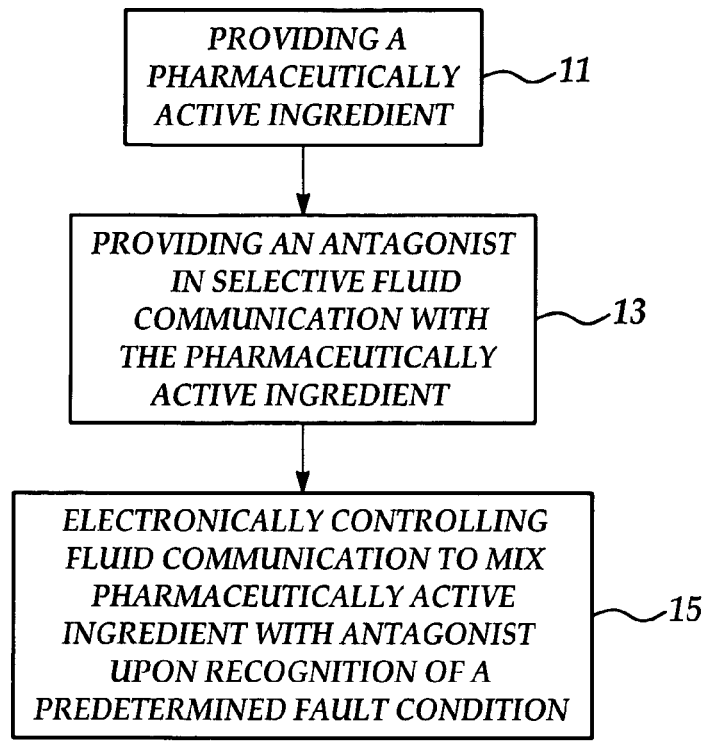
FIG. 1 is a flow diagram depicting an embodiment of a method of making a pharmaceutically active ingredient abuse-prevention device.

Referring now to FIG. 1, a flow diagram of an embodiment of a method of making a pharmaceutically active ingredient abuse-prevention device is depicted. A pharmaceutically active ingredient (e.g. a medicant) is provided, as shown at reference numeral 11. An antagonist of the pharmaceutically active ingredient is also provided such that the antagonist and the pharmaceutically active ingredient are in selective fluid communication with each other, as shown at reference numeral 13. The fluid communication is electronically (e.g. via electronic circuitry), and/or mechanically, selectively operatively controlled so that, upon recognition of a predetermined fault condition, the pharmaceutically active ingredient mixes with the antagonist, thereby rendering the pharmaceutically active ingredient substantially ineffective, as shown at reference numeral 15.

An alternate embodiment of the method (not depicted in FIG. 1) includes providing a pharmaceutically active ingredient in fluid communication with a drop generating device/member. An antagonist of the pharmaceutically active ingredient is also provided such that it is in selective fluid communication with the drop generating member. The fluid communication between the antagonist and the drop generating member is electronically, or mechanically, selectively operatively controlled so that, upon recognition of a predetermined fault condition, the antagonist is released to mix with the pharmaceutically active ingredient, thereby rendering the pharmaceutically active ingredient substantially ineffective.

It is to be understood that embodiment(s) of the method will be referred to in more detail in reference to FIGS. 2 through 5.

Figure 2:
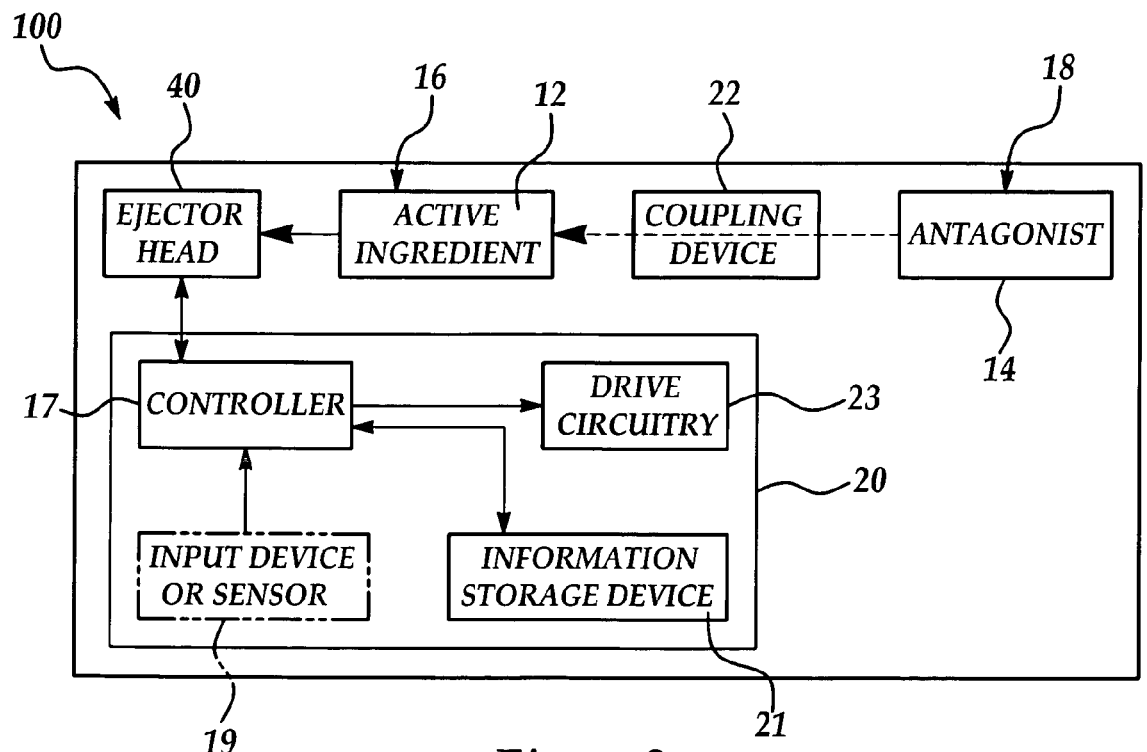
FIG. 2 is a schematic view of an embodiment of a system for preventing pharmaceutically active ingredient abuse.

Referring now to FIG. 2, a general embodiment of a system 100 for preventing pharmaceutically active ingredient abuse is depicted. It is to be understood that the large arrows generally represent fluid/selective fluid pathways, and that the small arrows generally represent electronic pathways.

The pharmaceutically active ingredient 12 (a non-limitative example of which is an opioid) and an antagonist 14 of the pharmaceutically active ingredient 12 are respectively contained in a reservoir 16 and a chamber/second reservoir 18. As depicted, the chamber 18 and the antagonist 14 are in selective fluid communication with, or are selectively fluidly coupled to, the reservoir 16 and the pharmaceutically active ingredient 12 contained therein.

Figure 4:
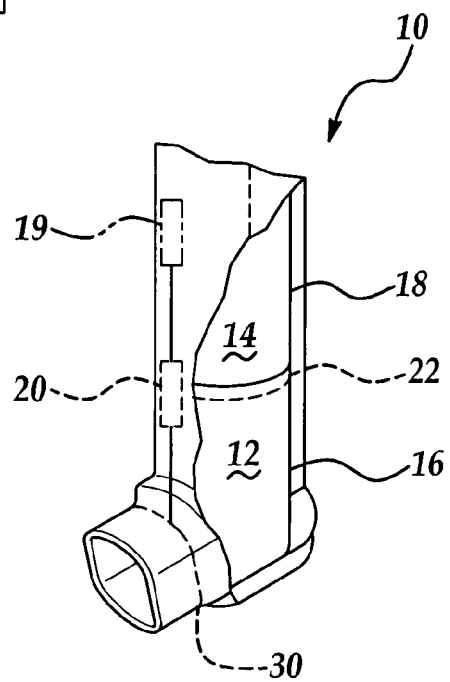
FIG. 4 is a perspective, semi-schematic cutaway view of an embodiment of an inhaler.
Figure 6:
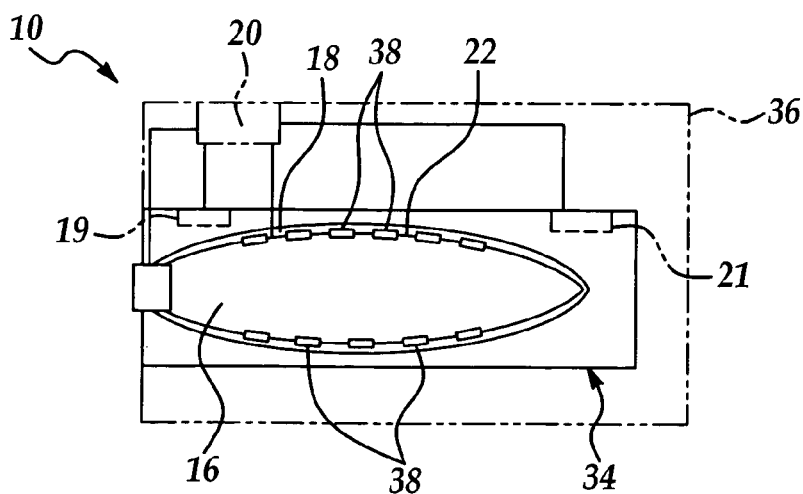
FIG. 6 is a semi-schematic view of an alternate embodiment of an inhaler.
Figure 7:
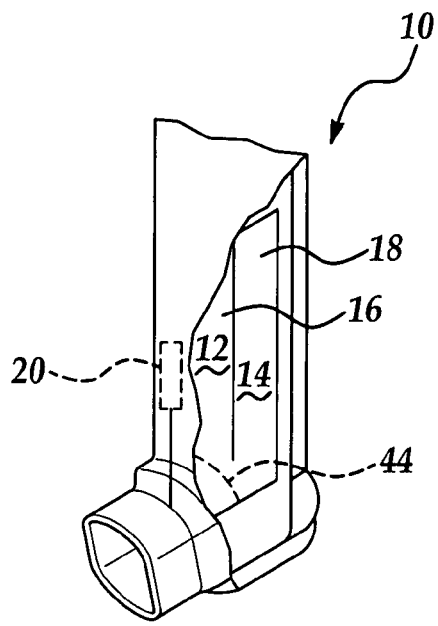
FIG. 7 is a perspective semi-schematic cutaway view of yet another embodiment of an inhaler.

It is to be understood that any suitable agonist/antagonist combination may be used in embodiments of the system 100, inhaler 10 (as shown in FIGS. 4, 6 and 7), and methods disclosed herein. In a non-limitative example, the opioid agonist fentanyl may be contained in the reservoir 16 and the antagonist naltrexone may be contained in the chamber 18.

The pharmaceutically active ingredient 12 may include those substances having the capacity to produce one or more of the following: a physical dependence in which withdrawal causes sufficient distress to bring about drug-seeking behavior; the ability to assuage withdrawal symptoms caused by withdrawal from other drugs; euphoria; and patterns of toxicity resulting from a dosage above a normal therapeutic range.

In a non-limitative embodiment, the pharmaceutically active ingredient is an opioid. The term "opioid" includes stereoisomers thereof, metabolites thereof, salts thereof, ethers thereof, esters thereof, derivatives thereof, and/or mixtures thereof. Non-limitative examples of opioids include anileridine, allylprodine, alfentanil, alphaprodine, benzylmorphine, buprenorphine, bezitramide, butorphanol, codeine, clonitazene, cyclazocine, dezocine, desomorphine, dihydromorphine, dextromoramide, diampromide, dihydrocodeine, diethylthiambutene, dimenoxadol, dimepheptanol, dimethylthiambutene, dipipanone, dioxaphetyl butyrate, eptazocine, ethylmorphine, ethylmethylthiambutene, etonitazine, ethoheptazine, fentanyl, hydrocodone, heroin, 6-hydroxymorphone, hydroxypethidine, hydromorphone, isomethadone, ketobemidone, levallorphan, levophenacylmorphan, lofentanil, levorphanol, morphine, myrophine, meperidine, meptazinol, metazocine, methadone, metopon, narceine, nalbuphine, nalorphine, nicomorphine, norlevorphanol, normethadone, normorphine, norpipanone, opium, oxycodone, oxymorphone, piritramide, papaveretum, pentazocine, phenadoxone, phenazocine, phenoperidine, piminodine, phenomorphan, propheptazine, promedol, properidine, propiram, propoxyphene, sufentanil, tilidine, tramadol, stereoisomers thereof, metabolites thereof, salts thereof, ethers thereof, esters thereof, and/or derivatives thereof, and/or mixtures thereof.

Non-limitative examples of antagonists include buprenorphine, cyclazocine, cyclophan, levallorphan, nalorphine, naltrexone, naloxone, nalmefene, nalbuphine, oxilorphan, pentazocine, and/or mixtures thereof.

In an embodiment, selective fluid communication/coupling between the reservoir 16 and the chamber 18 is controlled by electronic circuitry 20. In an example embodiment, electronic circuitry 20 includes a controller 17, an input or sensing device 19, a storage device 21 (e.g. a device capable of storing patient and other information), and/or drive circuitry 23. The controller 17 is configured to receive input from the input or sensing device 19; receive signals from, and send control signals to the ejector head 40 (described in reference to FIG. 8); exchange information with the storage device 21; and/or provide control signals to the drive circuitry 23.

It is to be understood that the input or sensing device 19 may be partially or substantially wholly incorporated into the electronic circuitry 20. The input or sensing device 19 is configured to impart a "fault" or "end state" condition signal to the controller 17 in the event that, for example, expiration, abuse, and/or exhaustion of the pharmaceutically active ingredient 12 occurs. It is to be understood that a "fault condition" may also be imparted within any portion of the electronic circuitry 20 or outside of the electronic circuitry 20. The input or sensing device 19 may include any or all of the following:

(a) A sensor configured to sense tampering of the inhaler 10 or system 100, such as an attempt to access the active ingredient 12. It is to be understood that the sensor may generate a signal that is passed to the controller 17 in the event of tampering.

(b) A sensor configured to sense the opening of an access door (not shown) in the inhaler 10 or system 100.

(c) A timer system configured to generate an expiration or fault signal upon reaching a certain time limit for use of the inhaler 10, system 100, and/or the active ingredient 12.

(d) A fluid level or volume indication system configured to provide an indication of an empty condition or fault condition when it is estimated or determined that the active ingredient 12 is no longer sufficient to allow proper operation of the inhaler 10 or system 100.

(e) A system for determining malfunction of one or more portions of the inhaler 10 or system 100.

In an embodiment, the controller 17 provides control signals to the ejector head 40 for control of any drop ejection elements in the ejector head 40. In an example embodiment, the ejector head 40 includes drop generator drive circuitry 20' (shown in FIGS. 8 and 9) that receives data, power, gate activation, fire-pulse, and/or other signals from the controller 17 for driving the drop generators 44 in the ejector head 40 depending, in part, on the specific electronic configuration of the ejector head 40. The controller 17 also receives signals from the ejector head 40 indicative of a state or condition of the ejector head 40, such as, for example, a temperature of a portion of the ejector head 40.

The storage device 21 stores a variety of information, such as, for example information indicative of an initial state of the inhaler 10 or system 100, a current state of the inhaler 10 or system 100, an amount of active ingredient 12 initially or remaining in the reservoir 16, whether a fault condition has occurred, and the like, and combinations thereof. In a non-limitative example, the storage device 21 is a non-volatile memory device. In other embodiments, the storage device 21 may include fusible links or other means for storing information.

It is to be understood that if a fault condition is imparted to the controller 17, the controller 17 applies signals to the drive circuitry 23 that in turn applies power signals to the coupling device 22 to enable mixing of the antagonist 14 with the pharmaceutically active ingredient 12.

Non-limitative examples of suitable predetermined fault conditions that the controller 17 may recognize include the following: system 100 or inhaler 10 tampering (non-limitative examples of which include removal or disassembly of the reservoir 16 and drilling into the reservoir 16), pharmaceutically active ingredient 12 expiration, pharmaceutically active ingredient 12 overuse or misuse, attempted re-use after system 100 or inhaler 10 disposal, unauthorized use, loss of back pressure, user request, and combinations thereof.

In response to receiving the one or more of the predetermined fault conditions, the controller 17 of the electronic circuitry 20 activates fluid communication between the reservoir 16 and the chamber 18 such that the pharmaceutically active ingredient 12 mixes with the antagonist 14, thereby rendering the pharmaceutically active ingredient 12 substantially ineffective. It is to be understood that the antagonist 14 is not released during normal operation of the system 100 (or inhaler 10), but rather is released upon recognition of the predetermined fault condition.

In an embodiment, a selectively actuated fluid coupling device 22 is operatively connected to the electronic circuitry 20 to achieve the selective fluid communication. In this embodiment, when a predetermined fault condition has been imparted, the electronic circuitry 20 actuates (e.g. opens, breaks, tears) the coupling device 22, which allows the antagonist 14 to mix with the pharmaceutically active ingredient 12. It is to be understood that any suitable selectively actuated fluid coupling device 22 may be used. Non-limitative examples of such coupling devices 22 include, but are not limited to electronic pumps, electronic valves, rupturable membranes (see FIG. 3), and/or the like, and/or combinations thereof.

In an alternate embodiment, selective fluid communication may be mechanically controlled. For example, a patient or a caregiver may actuate mixing prior to disposal of the device 10 or system 100. This may be accomplished via a mechanical member (a non-limitative example of which includes a switch) that operatively controls fluid communication between the reservoir 16 and the chamber 18.

Figure 3:
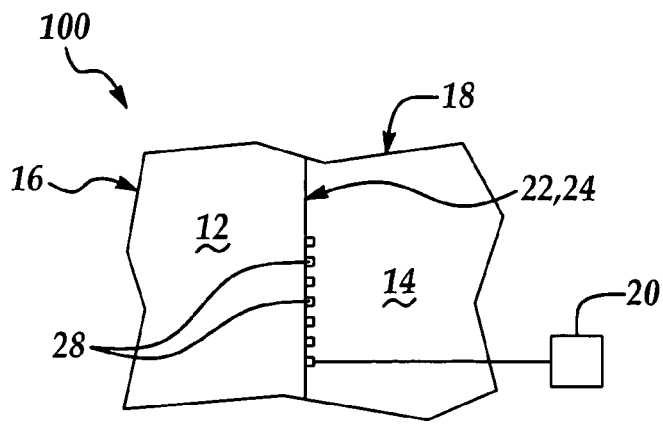
FIG. 3 is a schematic view of an alternate embodiment of a system for preventing pharmaceutically active ingredient abuse.

FIG. 3 depicts an embodiment of a system 100 with an embodiment of fluid coupling device 22 that is electronically controlled. This non-limitative example of the fluid coupling device 22 is a rupturable membrane or flexible wall 24. It is to be understood that this embodiment of the fluid coupling device 22 may be used in the system 100 or the inhaler 10 as described herein.

As depicted, the rupturable membrane 24 initially divides the reservoir 16 from the chamber 18. In an example embodiment, membrane 24 is a single or multilayer plastic film and includes a conductor and/or a wire pattern 28 operatively disposed thereon or therebetween. It is to be understood that incorporating the conductor and/or wire pattern 28 between the multiple layers of the membrane 24 may substantially prevent its exposure to reagents within the reservoir 16 and chamber 18 prior to membrane 24 rupture. The conductor and/or wire pattern 28 may have any suitable shape, geometry, and/or configuration as desired.

Non-limitative examples of suitable materials that make up the membrane 24 include polyethylene, oriented polyesters (for example polyethyleneterephthalate (PET)), evaporated metals, adhesion layers, polyvinylidene chloride (PVDC), ethylene vinyl alcohol (EVOH), and/or combinations thereof, and/or other such layers optimal for forming fluid barriers and/or for assembly. The membrane 24 may have any suitable thickness. Non-limitative examples of a suitable thickness range between about 10 μm and about 300 μm.

As depicted, the electronic circuitry 20 may be operatively connected to the conductor and/or wire pattern 28, such that upon recognition of a fault condition, the electronic circuitry 20 sends current through the conductor and/or wire pattern 28. The current heats the conductor and/or wire pattern 28, thereby causing the film of membrane 24 to rupture. As a result, the barrier between the antagonist 14 and the pharmaceutically active ingredient 12 is disabled, thereby mixing the two.

Referring now to FIG. 4, an embodiment of an inhaler 10 is depicted. The inhaler 10 includes a drop ejector 30 that releases a particular substance from within the inhaler 10 to, for example, a user's mouth, nose, etc. As such, the inhaler 10 may be a nasal inhaler and/or an oral inhaler (depicted in FIG. 4).

In an embodiment, the reservoir 16 (having the pharmaceutically active ingredient 12 disposed therein) and the chamber/second reservoir 18 (having the antagonist 14 disposed therein) are located within the inhaler 10. It is to be understood that the reservoir 16 is selectively fluidly coupled to the chamber 18, by, for example, fluid coupling device 22. As depicted, the chamber 18 is positioned over the reservoir 16. However, it is to be understood that the reservoir 16 and the chamber 18 may be positioned in any suitable manner/configuration such that they are selectively fluidly coupled. In a non-limitative example, the reservoir 16 and the chamber 18 may be positioned side by side within the inhaler 10. Further, the reservoir 16 and chamber 18 may take on any suitable shape, size, geometry, and/or configuration as desired. Non-limitative examples of suitable geometries include, but are not limited to cubic, cylindrical, pillow shaped, rounded, generally prismatic, and the like. Further, it is to be understood that the reservoir 16 and chamber 18 may be defined by rigid plastic walls, flexible plastic and/or metal films, rubber diaphragms, combinations thereof, and/or the like (non-limitative examples of which include those materials listed above in reference to membrane 24).

It is to be understood that the reservoir 16 is also in fluid communication with the drop ejector 30, such that the pharmaceutically active ingredient 12 may be released from the inhaler 10. It is to be further understood that, after a fault condition is recognized and a user attempts to use the inhaler 10, the user will inhale a mixture of the antagonist 14 and the pharmaceutically active ingredient 12, rendering the pharmaceutically active ingredient 12 substantially ineffective. Furthermore, the mixture of antagonist 14 and pharmaceutically active ingredient 12 is rendered substantially ineffective if administered by other routes, such as, for example, ingestion or injection.

An embodiment of the inhaler 10 includes the electronic circuitry 20 operatively controlling the fluid communication between the reservoir 16 and the chamber 18. It is to be understood that the electronic circuitry 20 may also control the drop ejector 30. In an embodiment, the drop ejector 30 is an element of a drop generating member 44 (see FIG. 8) that ejects a discrete droplet in response to receiving a current or voltage pulse. It is to be understood that the composition of the droplet released from the drop ejector 30 will be dependent on whether the electronic circuitry 20 has recognized a fault condition. Embodiment(s) of the drop ejector 30 will be described in further detail in reference to FIGS. 8 and 9.

In a non-limitative example embodiment, the drop ejector 30 of an oral inhaler releases discrete droplet(s) having diameter(s) ranging between about 1 μm and about 20 μm. For nasal inhalers, generally the discrete droplet(s) have diameters greater than about 20 μm.

In an embodiment, the inhaler 10 may optionally include an electronic sensing device 19 that is capable of sensing one or more predetermined fault conditions. In an embodiment, the sensing device 19 is operatively connected to the inhaler 10 and is in electrical communication with and/or forms a portion of the electronic circuitry 20. Upon sensing a fault condition, the electronic sensing device 19 may impart a signal to the controller 17 of the electronic circuitry 20, which in turn activates the selective fluid communication between the reservoir 16 and the chamber 18. It is to be understood that the electronic sensing device 19 may also be operatively connected to an embodiment of the system 100 as described herein.

The storage device 21 may store information pertaining to the inhaler 10 (or system 100), the patient, and/or the pharmaceutically active ingredient 12. Non-limitative examples of such information include an expiration date, identity of the patient, identity (e.g. serial number) of the reservoir 16, and whether the reservoir 16 had previously been installed elsewhere.

In the embodiment depicted in FIG. 5, sensing device 19 is a biometric input device that receives a signal carrying first information indicative of, for example, the identity of a person attempting to utilize inhaler 10 or system 100, as shown at reference numeral 31. The controller 17 of the electronic circuitry 20 may receive the activation signal generated by the sensing device 19, as shown at reference numeral 33. The storage device 21 has stored therein second information indicative of an authorized user of inhaler 10, and the controller 17 receives such information, as shown as reference numeral 35. The controller 17 of the electronic circuitry 20 compares this first information with the second information that is stored on or in the storage device 21, as at reference numeral 37. If the first information is found to not properly compare with the second information, a fault signal is then imparted to the controller 17, as shown at reference numeral 39. In response to the fault signal, the electronic circuitry 20 activates the coupling device 22 to allowing mixing of the antagonist 14 with the medicant 12. If however, the first information substantially matches the second information, an aerosol of the medicant 12 is generated, as shown at reference numeral 41.

Referring now to FIG. 6, a portion of an alternate embodiment of the inhaler 10 is schematically depicted. In this embodiment, the reservoir 16, the chamber 18, and optionally the sensing device 19 and the storage device 21 are contained within a cartridge 34 that is removable from a housing 36 that makes up the exterior of the inhaler 10. The housing 36 may contain an access door (not shown) for easy insertion and/or removal of the cartridge 34. When the cartridge 34 is disposed within the housing 36, it is to be understood that the electronic circuitry 20 may be configured such that it becomes operatively connected to the sensing device 19 (if present), the storage device 21 (if present), the fluid coupling device 22, and the drop ejector 30 (not shown).

FIG. 6 also depicts an example embodiment of the reservoir 16, chamber 18, and fluid coupling device 22. In this non-limitative embodiment, the reservoir 16 is a flexibly deformable inner member, while the chamber 18 is a flexibly deformable outer member that substantially surrounds the inner member. Non-limitative examples of the flexibly deformable members may be formed of flexible films, such as multilayer plastic films, plastic/metal films, and/or plastic/foil films, and combinations thereof. A selectively actuated fluid coupling device 22 separates the reservoir 16 from the chamber 28. In this embodiment, the fluid coupling device 22 is one or more plastic films having traces 38 disposed thereon or therebetween.

When a predetermined fault condition occurs, the controller 17 activates drive circuitry 23 that in turn passes sufficient current through traces 38 to melt or otherwise rupture the plastic films previously separating chamber 18 from reservoir 16, thereby fluidly coupling chamber 18 to reservoir 16.

In a non-limiting example, the electronic circuitry 20 may send current to the traces 38 when a user prematurely (e.g. prior to expiration of the pharmaceutically active ingredient 12) opens the access door (not shown) to remove the cartridge 34. In this example, a fault signal is generated any time the access door is opened after installation of the cartridge 34. In response to the fault signal, the controller 17 activates the drive circuitry 21 to pass current to traces 38. It is to be understood that if the fault signal is generated before the full use of the contents of reservoir 16, then this may be indicative of tampering or unauthorized attempts to access the pharmaceutically active ingredient 12 in reservoir 16.

Embodiment(s) of the system 100 and inhaler 10 as described herein may further include an additional means for sensing tampering. A conductor pattern (not shown) may be printed/placed on the reservoir 16, and the electronic circuitry 20 may be operatively connected thereto. It is to be understood that any sensing by the electronic circuitry 20 (e.g. sensing device 19), that the conductor pattern has been disrupted may trigger mixing of the antagonist 14 and the pharmaceutically active ingredient 14. A non-limitative example of the conductor pattern includes two metal layers on the reservoir 16. The electronic circuitry 20 may sense for shorting between these layers. Shorting may result from tampering with the inhaler 10. A non-limitative example of such tampering includes a puncture formed in the reservoir 16 by a user attempting to retrieve the pharmaceutically active ingredient 12.

FIG. 7 depicts an alternate embodiment of the inhaler 10, which uses drop generating technology to selectively form an aerosol mixture of the pharmaceutically active ingredient 12 and the antagonist 14, thereby rendering the pharmaceutically active ingredient 12 substantially ineffective. In this alternate embodiment, the reservoir 16 is in substantially consistent fluid communication with the drop ejector 30 (which is an element of drop generating member 44 and ejector head 44) and the chamber/second reservoir 18 is in selective fluid communication with the drop ejector 30. Selective communication between the drop ejector 30 and the chamber 18 may be accomplished via electronic control of drop generating member 44 (for example, the electronic controls determine from which reservoir 16, 18 the fluid(s) are withdrawn and sent to the drop ejector 30 or are withdrawn, mixed, and sent to the drop ejector 30).

It is to be understood that selective fluid communication between the drop ejector 30 and the chamber 18 generally means that the antagonist 14 is not released until the recognition of a predetermined fault condition.

Figure 8:
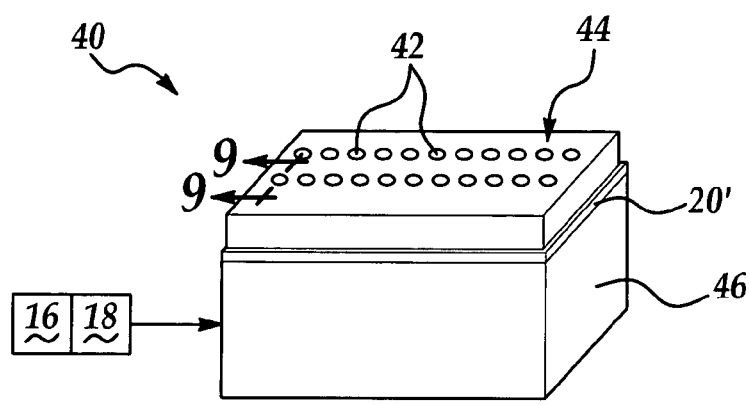
FIG. 8 is a schematic view of an embodiment of an ejector head from an embodiment of an inhaler.
Figure 9:
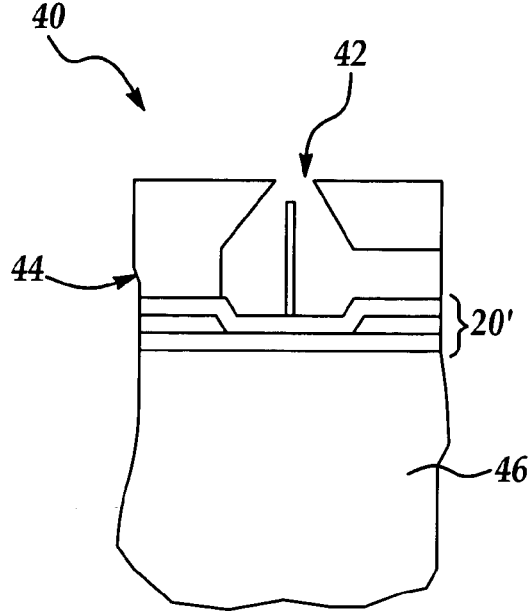
FIG. 9 is a cross-sectional semi-schematic view taken along line 9-9 of FIG. 8.

In an embodiment, the drop ejector 30 is an element of a drop generating member 44 which is incorporated into an ejector head 40 (shown in FIG. 8). The ejector head 40 is in fluid communication with the reservoir 16 and/or chamber 18 and is electronically controlled by the controller 17 of the electronic circuitry 20. Non-limitative examples of suitable ejector heads 40 include thermal drop ejection mechanisms, piezo drop ejection mechanisms, electrohydrodynamic drop ejection mechanisms, mechanical extrusion drop ejection mechanisms, and combinations thereof.

It is to be understood that the electronic circuitry 20 operates the release of the pharmaceutically active agent 12 under normal operation of the inhaler 10. Upon recognition of a fault condition or request, however, the electronic circuitry 20 activates fluid communication between the chamber/second reservoir 18 and the drop ejector 30. In an alternate embodiment, upon recognition of a predetermined fault condition or request, a user may mechanically activate the fluid communication between the chamber/second reservoir 18 and the drop ejector 30 via a switch. It is to be understood that, upon operation of the inhaler 10 after a fault condition or request has been recognized, both components 12, 14 are atomized by the ejector head 40 and released from the inhaler 10. As such, since both the antagonist 14 and the pharmaceutically active agent 12 are delivered from the inhaler 10, the pharmaceutically active agent 12 is rendered substantially ineffective.

Referring now to FIG. 8, an embodiment of an ejector head 40 is depicted. The ejector head 40 may include one or more drop generating members 44, which include the drop ejector 30 fluidly coupled to at least two reservoirs (e.g. the reservoir 16 and chamber 18), and at least one orifice 42 through which the droplet(s) is eventually ejected. The elements of the drop generator 44 may be electronically activated to release the fluid drops. It is to be understood that the drop generators 44 may be positioned as a linear or substantially non-linear array, or as an array having any two dimensional shape, as desired.

Drop generating circuitry 20' may be included in the ejector head 40. Non-limitative examples of drop generating circuitry 20' include thin film circuitry or a thin film device that define drop ejection elements, such as resistors or piezo-transducers. Still further, the drop generating circuitry 20' may include drive circuitry such as, for example, transistors, logic circuitry, and input contact pads. In one embodiment, the thin film circuitry includes a resistor configured to receive current pulses and to generate thermally generated bubbles in response. In another embodiment, the thin film circuitry includes a piezo-electric device configured to receive current pulses and to change dimension in response thereto.

It is to be understood that the drop generating circuitry 20' of the ejector head 40 may receive electrical signals and in response, may activate one or more of the array of drop generators 44. Each drop generator 44 is pulse activated, such that it ejects a discrete droplet in response to receiving a current or voltage pulse. Each drop generator 44 may be addressed individually, or groups of drop generators 44 may be addressed substantially simultaneously.

A non-limitative example of the ejector head 40 includes a substrate 46 having a plurality of drop generating elements 44 thereon. Any suitable substrate 46 may be selected and in a non-limitative embodiment, the substrate is one or more of single crystal silicon, polycrystalline silicon, silicon oxide containing dielectric substrates, alumina, sapphire, ceramic, glass, silicon wafers, plastics and/or combinations thereof.

FIG. 9 is a cross-sectional view taken along line 9-9 of FIG. 8, depicting an enlarged view of an orifice 42 and the drop generating member 44.

It is to be understood that the drop generating technology described herein may be used in combination with any of the embodiments discussed herein.

Embodiments of the system 100, inhaler 10, and methods disclosed herein offer many advantages, including, but not limited to the following. The fluid communication between either the reservoir 16 and the chamber 18 or the chamber 18 and the drop ejector 30 or ejector head 40 is advantageously controlled such that, upon exposure to and/or recognition of certain predetermined fault conditions, the pharmaceutically active ingredient 12 and antagonist 14 are mixed (either in the reservoirs 16, 18 and/or as the agents 12, 14 are being atomized and/or otherwise ejected from the inhaler 10 or system 100). Non-limitative examples of when the pharmaceutically active ingredient 12 may be rendered substantially ineffective include expiration of the ingredient 12, unauthorized use of the pharmaceutically active ingredient 12, tampering with the inhaler 10/system 100, etc. It is to be understood that when the pharmaceutically active ingredient 12 is rendered substantially ineffective (for example, through blocking of agonist receptor sites in the body by the antagonist 14), the antagonist 14 counteracts the effects of the pharmaceutically active ingredient 12 such that the user is advantageously substantially prevented from potentially abusing the pharmaceutically active ingredient 12.

While several embodiments have been described in detail, it will be apparent to those skilled in the art that the disclosed embodiments may be modified. Therefore, the foregoing description is to be considered exemplary rather than limiting.

What is claimed is:

1. An inhaler, comprising:

a drop ejector;

a housing;

a reservoir operatively disposed in the housing and in fluid communication with the drop ejector, the reservoir containing a pharmaceutically active ingredient;

a chamber containing an antagonist of the pharmaceutically active ingredient, the chamber operatively disposed in the housing and selectively fluidly coupled to the reservoir;

electronic circuitry operatively controlling the drop ejector and the fluid coupling of the chamber to the reservoir; and a cartridge removably disposed within the housing, the cartridge having disposed therein the reservoir, the chamber, and a sensing device adapted to be operatively connected to the inhaler and adapted to sense at least one predetermined fault condition;

wherein in response to obtaining information indicative of the at least one predetermined fault condition, the electronic circuitry renders the reservoir in fluid communication with the chamber such that the antagonist is mixed with the pharmaceutically active ingredient, thereby rendering the pharmaceutically active ingredient substantially ineffective.

2. The inhaler as defined in claim 1 wherein the sensing device is configured to selectively signal the electronic circuitry.

3. The inhaler as defined in claim 1 wherein the reservoir is a flexibly deformable inner member, the chamber is a flexibly deformable outer member surrounding the inner member, and a selectively actuated fluid coupling device is operatively disposed therebetween.

4. The inhaler as defined in claim 3 wherein the fluid coupling device comprises a plastic film having traces disposed thereon, the traces adapted to cause fluid connection between the inner member and the outer member upon receiving a predetermined signal from the electronic circuitry.

5. The inhaler as defined in claim 1 wherein the pharmaceutically active ingredient is fentanyl and the antagonist is naltrexone.

6. The inhaler as defined in claim 1 wherein the at least one predetermined fault condition includes at least one of inhaler tampering, pharmaceutically active ingredient expiration, pharmaceutically active ingredient overuse, attempted re-use after inhaler disposal, unauthorized use, user request, and combinations thereof.

7. The inhaler as defined in claim 1 wherein the inhaler is at least one of a nasal inhaler and an oral inhaler.

8. An inhaler, comprising:
a drop elector;
a reservoir in fluid communication with the drop ejector, the reservoir containing a pharmaceutically active ingredient;
a chamber containing an antagonist of the pharmaceutically active ingredient, the chamber selectively fluidly coupled to the reservoir;
electronic circuitry operatively controlling the drop elector and the fluid coupling of the chamber to the reservoir; and
a selectively actuated fluid coupling device which selectively fluidly couples the reservoir to the chamber, wherein the selectively actuated fluid coupling device is a ruptureable membrane that includes a film layer having at least one of a conductor and a wire pattern operatively disposed thereon;
wherein in response to obtaining information indicative of at least one predetermined fault condition, the electronic circuitry renders the reservoir in fluid communication with the chamber such that the antagonist is mixed with the pharmaceutically active ingredient, thereby rendering the pharmaceutically active ingredient substantially ineffective.

9. The inhaler as defined in claim 8 wherein the electronic circuitry includes at least one of a controller, a sensing device, drive circuitry, a storage device, and combinations thereof.

10. A method of making a pharmaceutically active ingredient abuse-prevention system, the method comprising:
providing a pharmaceutically active ingredient in a reservoir;
providing an antagonist of the pharmaceutically active ingredient in a chamber, the antagonist being in selective fluid communication with the pharmaceutically active ingredient and the chamber being selectively fluidly coupled to the reservoir;
configuring electronic circuitry to selectively operate the fluid communication so as to, upon recognition of at least one predetermined fault condition, mix the pharmaceutically active ingredient with the antagonist, thereby rendering the pharmaceutically active ingredient substantially ineffective; and
operatively removably disposing a cartridge in a housing configured to have the reservoir and chamber operatively disposed therein, the cartridge having disposed therein the reservoir, the chamber, and an electronic sensing device adapted to be operatively connected to the system and adapted to sense the at least one predetermined fault condition.

11. The method as defined in claim 10 wherein the antagonist is not released until recognition of the at least one predetermined fault condition.

12. The method as defined in claim 10 wherein the electronic sensing device is adapted to selectively signal the electronic circuitry.

13. The method as defined in claim 10, further comprising:
disposing the pharmaceutically active ingredient in the reservoir;
operatively and fluidly connecting the reservoir to a drop ejector; and
disposing the antagonist in the chamber, which is in selective fluid communication with the reservoir.

14. The method as defined in claim 10, further comprising:
disposing the pharmaceutically active ingredient in the reservoir;
operatively and fluidly connecting the reservoir to a drop ejector; and
disposing the antagonist in the chamber, which is in selective fluid communication with the drop ejector.

15. The method as defined in claim 10 wherein the reservoir is a flexibly deformable inner member, the chamber is a flexibly deformable outer member surrounding the inner member, and a selectively actuated fluid coupling device is operatively disposed therebetween.

16. The method as defined in claim 15 wherein the fluid coupling device comprises a plastic film having traces disposed thereon, and the method further comprises causing the traces to form a fluid connection between the inner member and the outer member.

17. The method as defined in claim 16 wherein causing the traces to form a fluid connection is accomplished by sending a predetermined signal to the traces from the electronic circuitry.

18. The method as defined in claim 10 wherein the at least one predetermined fault condition includes at least one of tampering, pharmaceutically active ingredient expiration, pharmaceutically active ingredient overuse, attempted re-use after disposal, unauthorized use, user request, and combinations thereof.

19. A method of making a pharmaceutically active ingredient abuse-prevention system, the method comprising:
providing a pharmaceutically active ingredient in a reservoir;
providing an antagonist of the pharmaceutically active ingredient in a chamber, the antagonist being in selective fluid communication with the pharmaceutically active ingredient and the chamber being selectively fluidly coupled to the reservoir;
operatively connecting a selectively actuated fluid coupling device such that the selectively actuated fluid coupling device accomplishes the selective fluid communication between the antagonist and the pharmaceutically active ingredient, wherein the selectively actuated fluid coupling device is a ruptureable membrane that includes a film layer having at least one of a conductor and a wire pattern operatively disposed thereon; and
configuring electronic circuitry to selectively operate the fluid communication so as to, upon recognition of at least one predetermined fault condition, mix the pharmaceutically active ingredient with the antagonist, thereby rendering the pharmaceutically active ingredient substantially ineffective.

20. A system for preventing pharmaceutically active ingredient abuse, comprising:
a housing;
a reservoir operatively disposed in the housing and containing a pharmaceutically active ingredient;
a chamber operatively disposed in the housing and containing an antagonist of the pharmaceutically active ingredient, the chamber selectively fluidly coupled to the reservoir;
electronic circuitry operatively controlling the fluid coupling; and
a cartridge removably disposed within the housing, the cartridge having disposed therein the reservoir, the chamber, and a sensing device adapted to be operatively connected to the system and adapted to sense at least one predetermined fault condition;
wherein in response to obtaining information indicative of the at least one predetermined fault condition, the electronic circuitry renders the reservoir in fluid communication with the chamber such that the antagonist is mixed with the pharmaceutically active ingredient, thereby rendering the pharmaceutically active ingredient substantially ineffective.

21. The system as defined in claim 20 wherein the sensing device is further adapted to selectively signal the electronic circuitry.

22. The system as defined in claim 20 wherein the reservoir is a flexibly deformable inner member, the chamber is a flexibly deformable outer member surrounding the inner member, and a selectively actuated fluid coupling device is operatively disposed therebetween.

23. The system as defined in claim 22 wherein the fluid coupling device comprises a plastic film having traces disposed thereon, the traces adapted to cause fluid connection between the inner member and the outer member upon receiving a predetermined signal from the electronic circuitry.

24. The system as defined in claim 20 wherein the pharmaceutically active ingredient is fentanyl and the antagonist is naltrexone.

25. The system as defined in claim 20 wherein the at least one predetermined fault condition includes at least one of system tampering, pharmaceutically active ingredient expiration, pharmaceutically active ingredient overuse, attempted re-use after system disposal, unauthorized use, user request, and combinations thereof.

26. A system for preventing pharmaceutically active ingredient abuse, comprising:
a reservoir containing a pharmaceutically active ingredient;
a chamber containing an antagonist of the pharmaceutically active ingredient, the chamber selectively fluidly coupled to the reservoir;
electronic circuitry operatively controlling the fluid coupling; and
a selectively actuated fluid coupling device which selectively fluidly couples the reservoir to the chamber, wherein the selectively actuated fluid coupling device is a ruptureable membrane that includes a film layer having at least one of a conductor and a wire pattern operatively disposed thereon;
wherein in response to obtaining information indicative of at least one predetermined fault condition, the electronic circuitry renders the reservoir in fluid communication with the chamber such that the antagonist is mixed with the pharmaceutically active ingredient, thereby rendering the pharmaceutically active ingredient substantially ineffective.

27. The system as defined in claim 26 wherein the electronic circuitry includes at least one of a controller, a sensing device, drive circuitry, a storage device, and combinations thereof.

28. An inhaler, comprising:
a drop ejector;
a housing;
a reservoir operatively disposed in the housing and in fluid communication with the drop ejector, the reservoir adapted to contain a pharmaceutically active ingredient;
a chamber adapted to contain an antagonist of the pharmaceutically active ingredient, the chamber operatively disposed in the housing and selectively fluidly coupled to the reservoir;
electronic circuitry operatively controlling the drop ejector and the fluid coupling of the chamber to the reservoir; and
a cartridge removably disposed within the housing, the cartridge having disposed therein the reservoir, the chamber, and a sensing device adapted to be operatively connected to the inhaler and adapted to sense at least one predetermined fault condition;
wherein in response to obtaining information indicative of the at least one predetermined fault condition, the electronic circuitry renders the reservoir in fluid communication with the chamber such that the antagonist is adapted to be mixed with the pharmaceutically active ingredient, thereby rendering the pharmaceutically active ingredient substantially ineffective.

* * * * *

UNITED STATES PATENT AND TRADEMARK OFFICE
CERTIFICATE OF CORRECTION

| | |
|---|---|
| PATENT NO. | : 7,827,983 B2 |
| APPLICATION NO. | : 11/017347 |
| DATED | : November 9, 2010 |
| INVENTOR(S) | : Douglas A. Sexton et al. |

It is certified that error appears in the above-identified patent and that said Letters Patent is hereby corrected as shown below:

In column 11, line 22, in Claim 8, delete "elector" and insert -- ejector --, therefor.

In column 11, line 29, in Claim 8, delete "elector" and insert -- ejector --, therefor.

Signed and Sealed this
Twentieth Day of December, 2011

David J. Kappos
*Director of the United States Patent and Trademark Office*